(12) United States Patent
Peine et al.

(10) Patent No.: US 7,378,856 B2
(45) Date of Patent: May 27, 2008

(54) ARRAY SENSOR ELECTRONICS

(75) Inventors: William Peine, Holliston, MA (US); Robert Pratico, Agoura Hills, CA (US); Jae S. Son, Rancho Palos Verdes, CA (US)

(73) Assignee: Pressure Profile Systems, Los Angeles, CA (US)

( * ) Notice: Subject to any disclaimer, the term of this patent is extended or adjusted under 35 U.S.C. 154(b) by 181 days.

(21) Appl. No.: 10/493,459

(22) PCT Filed: Oct. 24, 2002

(86) PCT No.: PCT/US02/34135

§ 371 (c)(1),
(2), (4) Date: Nov. 15, 2004

(87) PCT Pub. No.: WO03/036612

PCT Pub. Date: May 1, 2003

(65) Prior Publication Data

US 2005/0068044 A1 Mar. 31, 2005

Related U.S. Application Data

(60) Provisional application No. 60/347,599, filed on Oct. 24, 2001, provisional application No. 60/343,714, filed on Oct. 24, 2001.

(51) Int. Cl.
*G01R 27/26* (2006.01)
(52) U.S. Cl. ...................... 324/662; 324/661; 324/686
(58) Field of Classification Search ............... 324/661, 324/662, 686, 688, 616
See application file for complete search history.

(56) References Cited

U.S. PATENT DOCUMENTS

| | | | | |
|---|---|---|---|---|
| 4,021,625 | A | * | 5/1977 | Bradley .................... 379/22.02 |
| 4,526,043 | A | | 7/1985 | Boie et al. |
| 5,055,838 | A | * | 10/1991 | Wise et al. ............. 340/870.37 |
| 5,148,126 | A | * | 9/1992 | Spencer ....................... 331/135 |
| 5,373,245 | A | * | 12/1994 | Vranish ....................... 324/662 |
| 5,905,209 | A | * | 5/1999 | Oreper ................... 73/862.045 |
| 5,942,733 | A | | 8/1999 | Allen et al. |
| 6,312,061 | B1 | * | 11/2001 | Schliebe et al. .............. 303/20 |
| 6,937,031 | B2 | * | 8/2005 | Yoshioka et al. ........... 324/662 |
| 2003/0194984 | A1 | * | 10/2003 | Toncich et al. ............. 455/323 |

OTHER PUBLICATIONS

Sergio et al., "A System-On-Chip for Pressure-Sensitive Fabric," IEEE Custom Integrated Circuits Conference 2001, pp. 413-416.

(Continued)

*Primary Examiner*—Andrew H. Hirshfeld
*Assistant Examiner*—Amy He
(74) *Attorney, Agent, or Firm*—Wolf, Greenfield & Sacks, P.C.

(57) ABSTRACT

Circuits and methods for detecting and amplifying sensor and sensor array (102, 104) output signals are presented. According to some aspects, a nonlinear feedback loop containing a sensor element provides a nonlinear transformation that compensates for a corresponding nonlinear response of the sensor element thereby providing a linearized final output signal. In other aspects, idle sensors are coupled to a reference on non-idle sensor elements. Other aspects include sensor and amplification circuits which operate without traditional filtering or switching elements, such that a higher throughput is achieved and no settling time is required due to traditional transients, thus allowing for faster scanning of larger sensor arrays. Some embodiments of the present invention are directed to variable gap capacitive sensor arrays and the signal processing electronics.

29 Claims, 8 Drawing Sheets

OTHER PUBLICATIONS

Baxter, "Capacitive Sensors," IEEE (Table of Contents).
Document downloaded on Sep. 20, 2006 from website: http://www.ieee-cicc.org/2001/conference/program/tp.html.
Document downloaded on Sep. 20, 2006 from website: http://www.ieee-cicc.org/2001/conference/program/tp6.html.#session20.
Document downloaded on Sep. 20, 2006 from website: http://www.ieee-cicc.org/2001/general/registration.html.
Jae S. Son, "*Integration of Tactile Sensing and Robot Hand Control*", Thesis from Harvard University, May 1996.

* cited by examiner

ARRAY SENSOR ELECTRONICS

RELATED APPLICATIONS

This application claims priority under 35 U.S.C. § 119(e) to co-pending U.S. Provisional Patent Application Ser. No. 60/347,599, entitled "CAPACITIVE ARRAY SENSOR ELECTRONICS," filed on Oct. 24, 2001. This application further relates to co-pending U.S. Provisional Patent Application Ser. No. 60/343,714, entitled "TIME SPATIAL VISUALIZATION OF LINEAR ARRAY DATA," filed on Oct. 24, 2001. This application also relates to a co-pending U.S. patent application Ser. No. 10/281,068 entitled "VISUALIZATION OF VALUES OF A PHYSICAL PROPERTY DETECTED IN AN ORGANISM OVER TIME," filed on even date herewith. Each of the above-cited applications is hereby incorporated by reference in its entirety.

TECHNICAL FIELD

The present application relates to sensor systems such as capacitive array sensors. More particularly, the present application relates to circuits and systems for capturing, amplifying and processing signals received from sensors and sensor arrays.

BACKGROUND

Sensors are devices that respond to a stimulus and produce a signal indicative of the stimulus' magnitude or other characteristic related to the stimulus. The stimulus may be any physical quantity or parameter which can affect a sensor and is usually a measurable parameter or effect. An array of sensors is a collection of individual sensors that are positioned at discrete locations and are related to one another in at least some aspects.

Sensor arrays are used in applications such as imaging, and generally involve a plurality of individual sensors placed in relation to one another such that an effectively larger sensor is formed by the array of sensors. That is, when placing sensors at a plurality of discrete locations over a region of interest it is possible to make some determination or estimate of the stimulus over the entire region of interest. Extrapolation or interpolation can provide an estimate of the magnitude of the stimulus at a spot which does not itself contain a discrete sensor. Furthermore, aggregate measures of the stimulus over the entire region of interest or smaller regions within the region of interest may be obtained by averaging or other operations performed on signals derived from individual sensors.

Applications in which such sensor arrays are useful include touch pads and distributed sensors that provide an indication of the location and magnitude of a force or a pressure applied to a region of interest.

One type of sensor array is a capacitive sensor array. This array employs a number of discrete capacitors distributed over a region of the array which may be arranged in a pattern forming a grid. A grid of sensors may comprise a plurality of capacitive sensors which may be individually addressable or addressable in groups or in their entirety. Addressing specific sensors may be accomplished using multiplexers coupled to the sensor array according to data or select signals on multiplexer select lines to determine the individual sensors to be driven or sampled. By driving a sensor it is meant the process of generally exciting the sensor or energizing the sensor so as to produce a measurement of the stimulus at the sensor. By sampling a sensor it is meant receiving an output signal from the sensor to read or detect the sensor response to the stimulus. Thus, it is possible to selectively measure a signal from a given capacitive sensor element located at a particular column and row of the capacitive array. Multiplexers may be used to determine the particular row and column from which a measurement is desired.

Capacitive array sensors have been constructed of rows and columns of conductive strips separated by a dielectric material. FIG. 1 illustrates a capacitive array 100 having conductive strips arranged along rows 102 and columns 104. The rows 102 and columns 104 of the capacitive array 100 may be separated by a flexible deformable material such as a silicone gel. The silicone gel (not shown) will deform in response to pressure applied to a surface of the capacitive array 100. The deformation of the silicone gel or other flexible substance can cause the rows 102 and columns 104 of the capacitive array 100 to become nearer or more distant to one another. Gap distance (d) is a factor which determines the capacitance of the capacitors 200 formed by ah intersection of the rows 102 and columns 104 of the capacitive array 100. If the rows 102 and columns 104 of the capacitive array 100 are coupled to electrical connections and to an external circuit, the capacitance of each of the capacitors 200 formed by the intersection of the rows 102 and columns 104 can be measured individually.

A sensor array can be driven and sampled, one sensor at a time or in groups, or in its entirety. By scanning the capacitive array 100 to obtain a signal or measurement from each of its individual elements 200, it is possible to form a real-time picture of the pressure applied to the capacitive array 100.

FIG. 2 illustrates a single capacitive array element 200. The element 200 is formed by an intersection of a row 102 and a column 104 of the capacitive array 100. The figure illustrates a distance or gap (d) that separates the row 102 and column 104 conductive strips. The capacitance of the capacitor 200 is generally proportional to the area formed by the intersection of the row 102 and column 104 divided by the distance d. Hence, changes in the distance d result in changes in the value of the capacitor 200. The relationship between the capacitance of the capacitor 200 and the stimulus, e.g., applied pressure, may be nonlinear for a variety of reasons. These reasons include the deformation response of the flexible deformable material, e.g., the silicone gel, as well as other physical and electrical responses of the variable gap capacitance element 200.

For large arrays, technical challenges arise in making fast measurements or scans of the entire sensor array. For example, a sampling circuit such as a multiplexer that samples a selected row and column on which to perform a measurement would have to cycle through all rows and all columns (all elements of the array) at a rate sufficient to provide the measurements as required by the specific application.

Nonlinear responses in the signals derived from the individual capacitors and the stimulus, e.g., applied pressure, complicate the design of an overall sensor circuit. Furthermore, the measured signal is typically small compared to the driving signal which drives the capacitive array. This results in a poor signal-to-noise ratio when attempting to derive a useful modulation signal reflecting the quantity being measured. This is because noise becomes amplified as well as the signal being measured when using simple signal amplification.

Traditional sensor circuits employ filters and switches that slow acquisition times by causing transients which need to decay between acquiring measurements from the various elements of an array. For example, in scanning a sensor array, a switch switches between the individual sensors of a traditional array, causing a transient signal to occur. Not only do transients slow the acquisition of a complete sensor array scan, but they can affect the quality of a measurement of a stimulus by introducing noise into sensed signals.

Furthermore, conventional sensor arrays contain considerable parasitic capacitances between sensor elements and other parts of the circuit, such as ground. These parasitic capacitances can contaminate sensed signals with noise and extraneous signal components and can require extra filtering circuitry and processing time to compensate for the parasitic capacitance.

SUMMARY

Aspects of one embodiment of the present invention are directed to a sensor system, comprising a sensor array having a plurality of sensor elements; at least one sensor element of the sensor array, having addressable connections designating the sensor element, that senses a stimulus; and an amplifier, disposed in a feedback arrangement around the sensor element, the amplifier receiving an input signal corresponding to an output of the sensor element and providing an output signal that drives the sensor element.

Another embodiment comprises aspects directed to a method for measuring a stimulus on a sensor array, comprising sensing the stimulus using at least one sensor element of the sensor array; generating a sensor element output signal corresponding to the sensed stimulus; amplifying the sensor element output signal to generate an amplified signal representative of the physical property; and feeding back the amplified signal to drive the sensor element.

Still another embodiment comprises aspects directed to a method for linearizing a non-linear sensor response, comprising sensing a stimulus using a sensor element; generating a sensor output signal corresponding to the stimulus; feeding back the sensor output signal to an input of the sensor through a non-linear transformer feedback loop corresponding to the non-linear sensor response.

Another embodiment of the invention comprises aspects directed to a method for reducing parasitic capacitance in a capacitive sensor array, comprising selectively coupling at least one sensor element in the sensor array to a common potential during a time period in which the sensor element is idle.

BRIEF DESCRIPTION OF THE DRAWINGS

In the drawings, each similar component that is illustrated in various figures is represented by a like numeral, although this does not necessarily signify that the components are identical. For purposes of clarity, not every component may be labeled in every drawing. In the drawings.

DETAILED DESCRIPTION

The present description describes various aspects of preferred embodiments of the invention. Some aspects have been described in other co-pending applications. Specifically, this application claims priority under 35 U.S.C. § 119(e) to co-pending U.S. Provisional Patent Application Ser. No. 60/347,599, entitled "CAPACITIVE ARRAY SENSOR ELECTRONICS," filed on Oct. 24, 2001. This application further relates to co-pending U.S. Provisional Patent Application Ser. No. 60/343,714, entitled "TIME SPATIAL VISUALIZATION OF LINEAR ARRAY DATA," filed on Oct. 24, 2001. This application also relates to a co-pending U.S. patent application Ser. No. 10/281,068 entitled "VISUALIZATION OF VALUES OF A PHYSICAL PROPERTY DETECTED IN AN ORGANISM OVER TIME," filed on even date herewith. Each of the above-cited applications is hereby incorporated by reference in its entirety.

The present invention is not limited in its application to the details of construction and the arrangement of components set forth in the following detailed description of the preferred embodiment and drawings. Rather, the invention encompasses other embodiments and may be practiced and carried out in various ways. Also, the terminology used herein is for the purpose of description and should not be regarded as limiting when used to describe aspects and embodiments of the invention. The use of "including," "comprising," or "having," "containing," etc., and variations thereof are meant to be open-ended and encompass at least the items listed thereafter.

Figure 1:
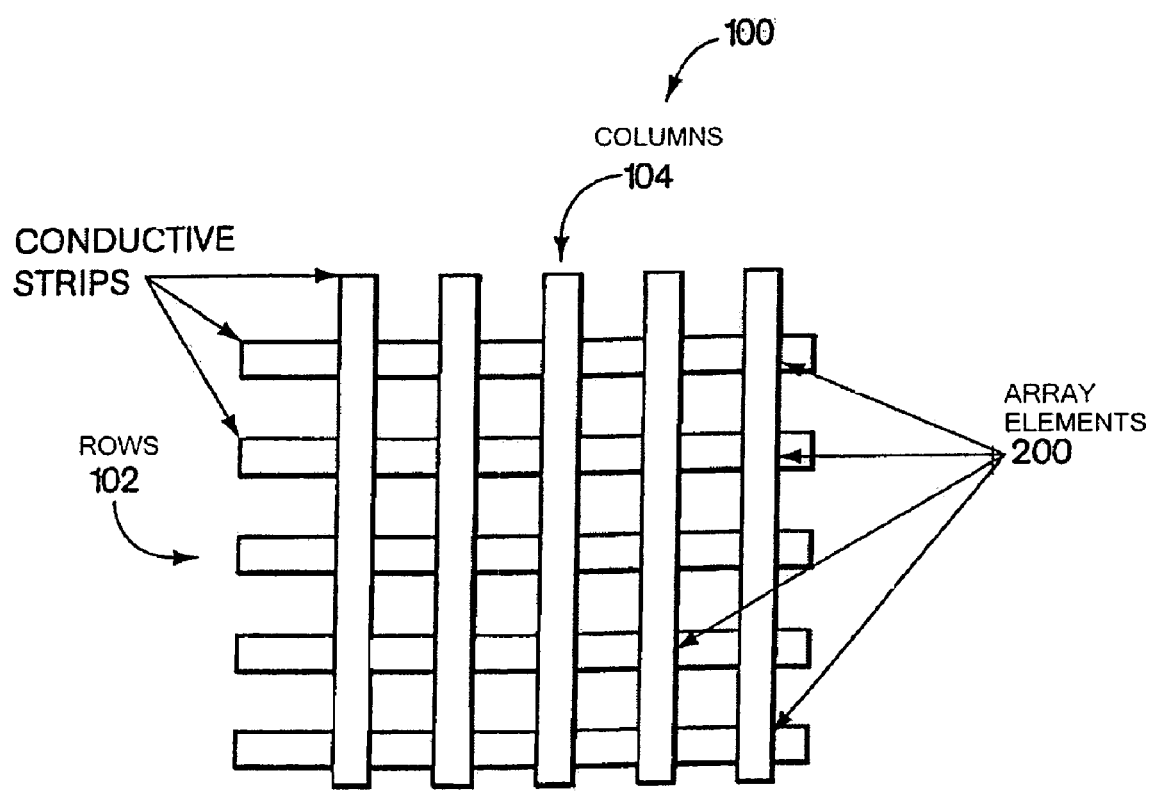
FIG. 1 illustrates an overview of a capacitive sensor array having several rows and columns of conducting strips.
Figure 2:
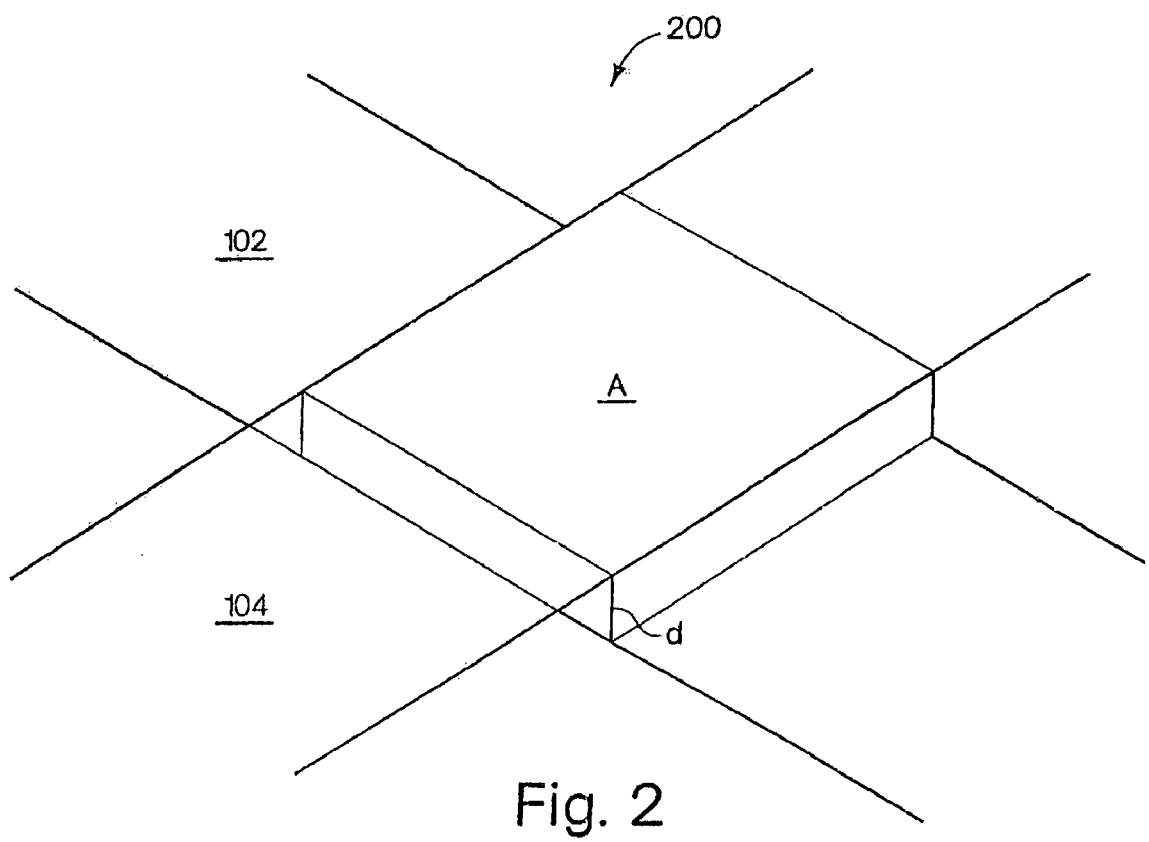
FIG. 2 illustrates an overview of a sensor element formed by the overlap of two conducting strips separated by a dielectric gap of size (d)
Figure 3:
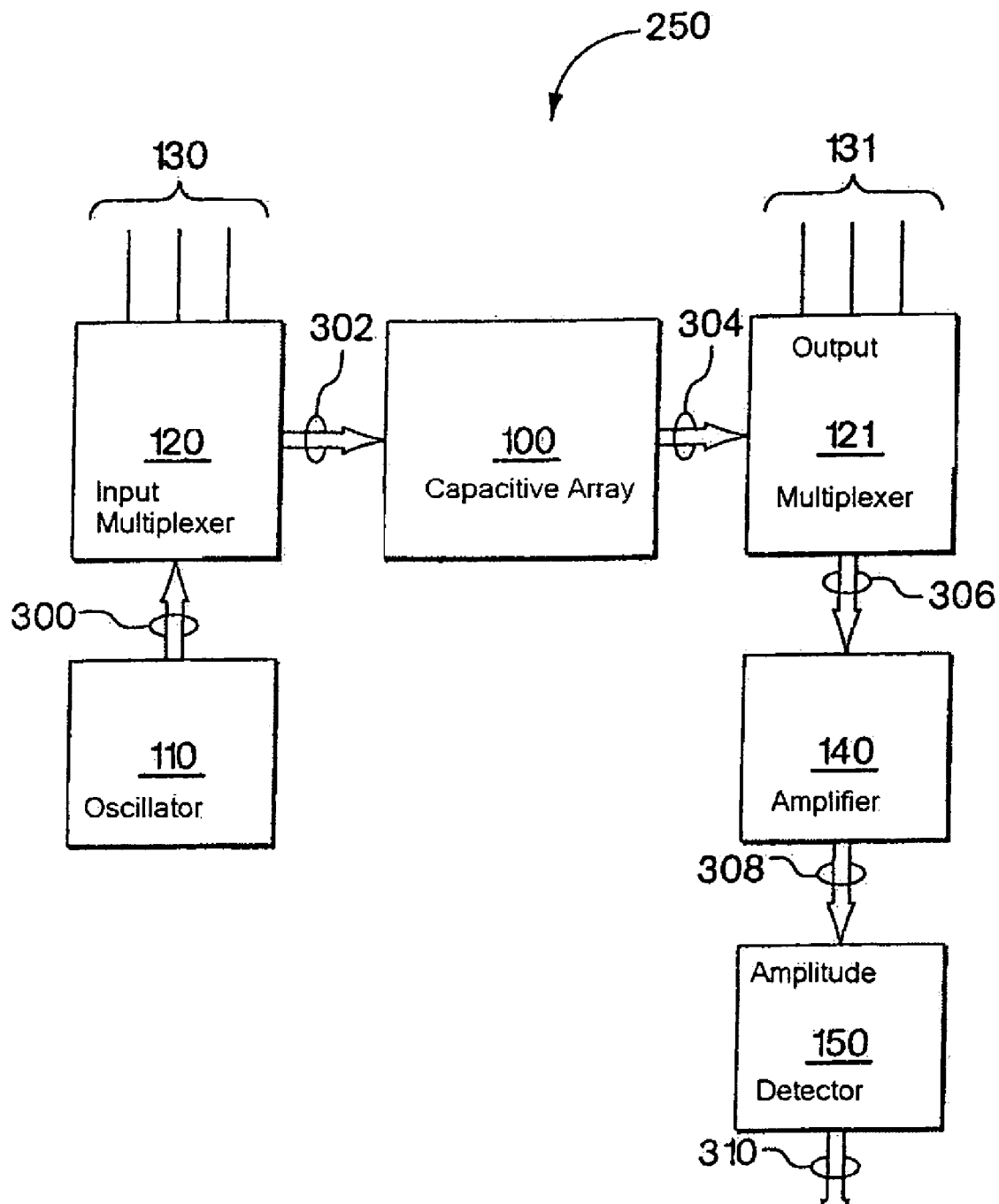
FIG. 3 illustrates a schematic representation of an exemplary system for driving and sampling a sensor array and amplitude detection.

FIG. 3 illustrates aspects of a capacitive array scanning system 250 used to drive and sample a capacitive array 100. An oscillator 110 provides an oscillator signal 300 to an input multiplexer (MUX) 120 which selects from the elements of capacitive array 100 one or more elements to be driven by at least the oscillator signal 300. Selection of the one or more elements to be driven is made using data on the input select lines 130. By proper identification of the individual or group of elements to be driven, a voltage or current may be supplied to selected sensor elements 200 as described previously. Oscillator signal 300 may be one of a plurality of signals driving elements 200.

Array input signal 302 provides a driving signal which is delivered to selected sensor elements 200. Once excited or driven by the array input signal 302, the capacitive array provides an array output signal 304. An output multiplexer 121 receives the array output signal 304 and, depending on the data provided to output select lines 131, the output multiplexer 121 provides a selected signal 306. Again, the selected signal 306 may comprise one or more selected samples from the capacitive array 100.

In some embodiments, the selected signal 306 be amplified by an amplifier 140. The amplifier 140 may be of any type, including analog or digital types, that provides an amplified signal 308. According to some aspects, amplification of the selected signal 306 improves resolution and accuracy of the measurement of the stimulus. An amplifier 140 may provide any gain, including gains greater than or less than unity and unity gains. The amplified signal 308 is therefore not constrained to be a signal having an amplitude greater than the selected signal 306.

The amplified signal 308 is detected by an amplitude detector 150, which is typically matched to the range of expected amplitudes provided in the amplified signal 308. Note that some embodiments may employ transconductance amplifiers, energy converters, or other elements that convert one type of signal into another. For example, an electrical signal such as a voltage may be converted into a corresponding optical signal.

The amplitude detector 150 may be any suitable amplitude detector that may detect the size, strength or amplitude of a signal. For example, the amplitude detector 150 may comprise a voltage-measuring circuit or a current-measuring circuit or a frequency measuring circuit, together described herein as amplitude detectors for the sake of simplicity. It should be appreciated that the amplifier 140 may amplify any type of characteristic of the selected signal 306 and that the amplified signal 308 merely indicates that characteristic is enhanced to generally make it simpler to read or measure the characteristic. As mentioned, the amplitude of an alternating current (AC) voltage signal may be a convenient characteristic to amplify and measure using the amplitude detector 150, however, the present invention is not so limited.

The amplitude detector 150 provides a detector output signal 310 corresponding to the amplified signal and in turn corresponding to the selected signal obtained from the element or elements of the capacitive array 100.

It is to be appreciated that FIG. 3 is merely one schematic embodiment of a capacitive array scanning system, and that various configurations and equivalent circuits may be constructed accordingly. Other auxiliary elements and circuit components, not described herein, may be used in various applications and embodiments, depending on the need at hand. For example, filters such as high-pass filters, band-pass filters and low-pass filters may reduce unwanted noise or provide other signal conditioning functions to the overall scanning system 250. Furthermore, signal processing techniques, implemented in hardware and/or software may be used at one or more positions in the scanning system 250 to add or remove spectral characteristics or other features to or/from the various signals described above.

Figure 4:
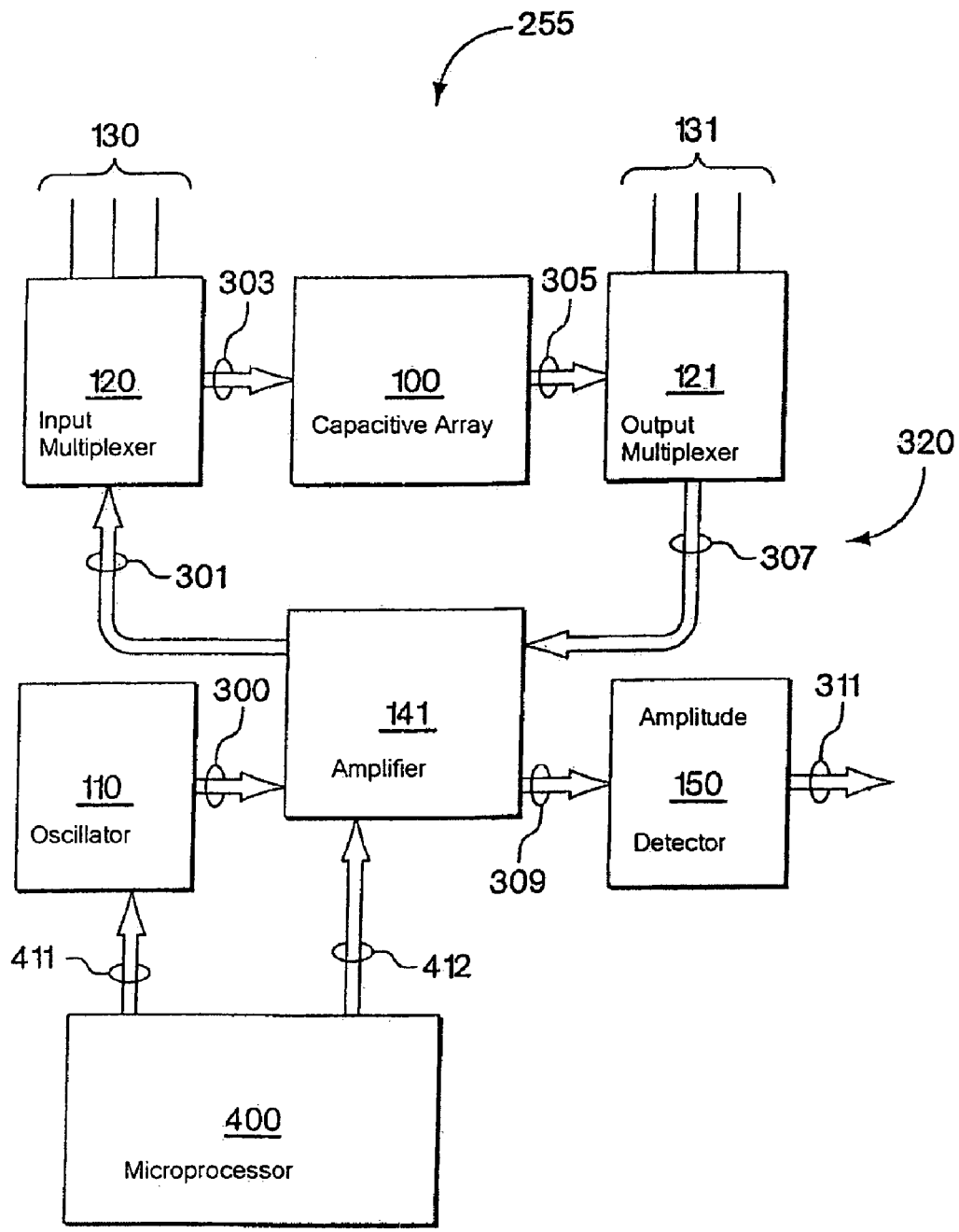
FIG. 4 illustrates a schematic representation of an exemplary system for driving and sampling a sensor array, including a feedback loop.

FIG. 4 illustrates an embodiment showing aspects of the present invention used in a capacitive array scanning system 255. Again, the scanning system is not limited in applicability to the capacitive array sensors described herein, but is more generally applicable to other types of sensors as well. The scanning system 255 comprises a feedback loop 320, which in some embodiments provides a linearizing function, as will be described below.

An oscillator 110 provides an oscillator signal 300 to amplifier 141. The amplifier 141 amplifies the oscillator signal 300 and provides an amplified input signal to input multiplexer 120, sometimes referred to as a driving multiplexer (DMUX). The input multiplexer 120 receives the amplified input signal 301 as well as data on input select lines 130, as described earlier. The array input signal 303 is provided by the input multiplexer 120 to selectively drive array element members 200 (not shown) of the capacitive array 100. The capacitive array 100 is driven or excited selectively by the array input signal 303, as was described above. An array output signal 305 is provided from the capacitive array 100 to an output multiplexer 121, sometimes referred to as a sampling multiplexer (SMUX). The output multiplexer 121 samples the selected array elements according to the data on output sampling lines 131.

The output multiplexer 121 provides a selected signal 307 back to the amplifier 141. In this way, the amplifier 141, the capacitive array 100 and other elements, are arranged in a feedback loop 320 by which the amplified input signal 301 and the selected signal 307 act to return a portion of the capacitive array's output to its input. In the embodiment of FIG. 4, input and output multiplexers, 120 and 121 respectively, are the elements to which and from which the feedback loop 320 couples the amplifier 141 and the capacitive array 100.

The selected signal 307, once provided to amplifier 141 is also amplified and provided as an amplified output signal 309 to amplitude detector 150. In some embodiments, signals 301 and 309 are the same or have the same value. The amplitude detector 150 provides a detector output signal 311, similar to that which was discussed with regard to FIG. 3. Again, the exact embodiment disclosed in FIG. 4 is not limiting, but may be adapted and substituted with one or more elements or auxiliary circuits, filters, amplifiers, etc., as called for by the application at hand.

It is also to be appreciated that the arrangement shown in the present embodiment does not depict a physical layout of the elements of the scanning system. For instance, some elements of the scanning system 255 may be implemented on remote circuits, as opposed to being implemented on the same circuit. Also, the entire scanning system 255 may be implemented on a microchip or other integrated circuit that performs the scanning system's function. Furthermore, various functions of the scanning system 255 may be carried out in software or in firmware or in any combination of hardware and software suitable. Examples include digital signal processing (DSP) hardware and/or software to perform various functions, e.g. filtering and amplification and application-specific integrated circuits (ASICs).

The oscillator 110 provides an output voltage signal such as an AC waveform. In some embodiments, the oscillator output signal 300 substantially comprises a single frequency sinusoid. The oscillator 110 may be free-running or may be used in a burst mode depending on the application. According to some aspects of the invention, the amplitude and/or frequency of the oscillator output signal 300 may be altered to improve measurement quality or scan rate or another operating parameter of the scanning system 255. Furthermore, the oscillator 110 may be replaced by another suitable component that can provide a periodic driving signal in a steady or pulsed or programmed mode. One example may be to replace the oscillator 110 with a microcontroller or other digital processing control unit that provides a signal substantially equivalent to that described as the oscillator output signal. The oscillator 110 may be controlled by a microprocessor 400 that supplies a control signal 411.

The input multiplexer 120 and the output multiplexer 121 may be of substantially similar design in some aspects of the present invention. According to some embodiments, the multiplexers 120, 121 select a single row 102 and column 104 from the capacitive array 100. This selection designates a single element 200 of the array 100. However, the input and output multiplexers 120, 121 may also be used to select multiple rows and columns simultaneously.

Multiplexer designs having a fast settling time are preferred in some embodiments because they allow for fast switching between sensor elements at a high sampling rate, thus improving the overall bandwidth for the scanning system 255.

The data on the input select lines 130 and the output select lines 131 of the multiplexers 120 and 121 respectively, may be provided in a number of ways. For example, the selection lines 130 and 131 may be set by a microcontroller or digital signal processing unit 400 and may also be set to increment automatically as would be done with a finite state machine. Additionally, separate amplifiers may be included in either or both of the multiplexers 120 and 121 at any of the inputs and outputs of said multiplexers. Also, an amplifier may be constructed as part of the multiplexing scheme used by the multiplexers 120 and 121.

According to some aspects of the present invention, placing the amplifier 141 in the feedback loop 320 comprising the capacitive array 100 and the multiplexers 120 and 121, allows for a higher gain and thus a higher sensitivity in the overall scanning system 255.

Amplifiers 140 and/or 141 may be implemented as described above and can also include provisions for adjusting the gain and offset of said amplifiers. Said gain and offset of amplifiers 140 and/or 141 may be prescribed on an element-to-element basis or as a single setting suitable for all elements. That is, the amplification gain or scheme used for each individual sensor element may be individually tailored to that element, or the gain may be held constant for the entire array 100. An approach combining the element-to-element setting and the single setting for all elements may be used as appropriate. A microcontroller or digital signal processing unit 400 may control said offset and gain corrections for best overall results using control signal 412.

FIG. 4 illustrates a microcontroller or digital signal processing unit 400 which provides control signals 411 and 412 to the oscillator 110 and to the amplifier 141, respectively. The microcontroller 400 may be implemented in hardware or in software or in a combination of hardware and software, including a DSP component, as best suits the application at hand.

The amplitude detector 150 samples the selected signal 307 at a sampling rate which is typically greater than the array scan rate. According to one embodiment, if a 10 by 10 array is scanned at 100 Hz, then the scan rate is 10 kHz. In this embodiment, the amplitude detector 150 would complete individual measurements at a rate greater than 10 kHz.

According to some embodiments of the present invention, the amplitude detector 150 is implemented using a rectifier that rectifies the output of the output multiplexer 121, thereby acting as a nonlinear transformer. The nonlinear transformation achieved thereby may be subsequently augmented by integrating the resulting transformer output signal over an integer number of periods. In one embodiment the integration is carried out over 10 cycles.

The nonlinear transformation mentioned above may comprise a function that creates a DC component in the signal proportional to the amplitude of the sensed signal 305 or the selected signal 307. While not recited herein for purposes of limitation, examples of such nonlinear transformation include full-wave or half-wave rectification, phase-corrected multiplication with the original driving AC signal, as well as multiplying the output signal with itself to obtain the output signal squared. The amplitude detector 150 may further comprise a root-mean-square (RMS) measuring circuit, a peak detector circuit an envelope detector circuit, or an amplitude modulation circuit and a low-pass filter circuit. Amplitude detection could also be accomplished in some embodiments by sampling the AC waveform using an analog to digital (A/D) converter and using a digital signal processor or microcontroller to compute the measured signal amplitude from the sampled data. As mentioned above, both digital and analog methods may be used for amplitude detection.

Figure 5:
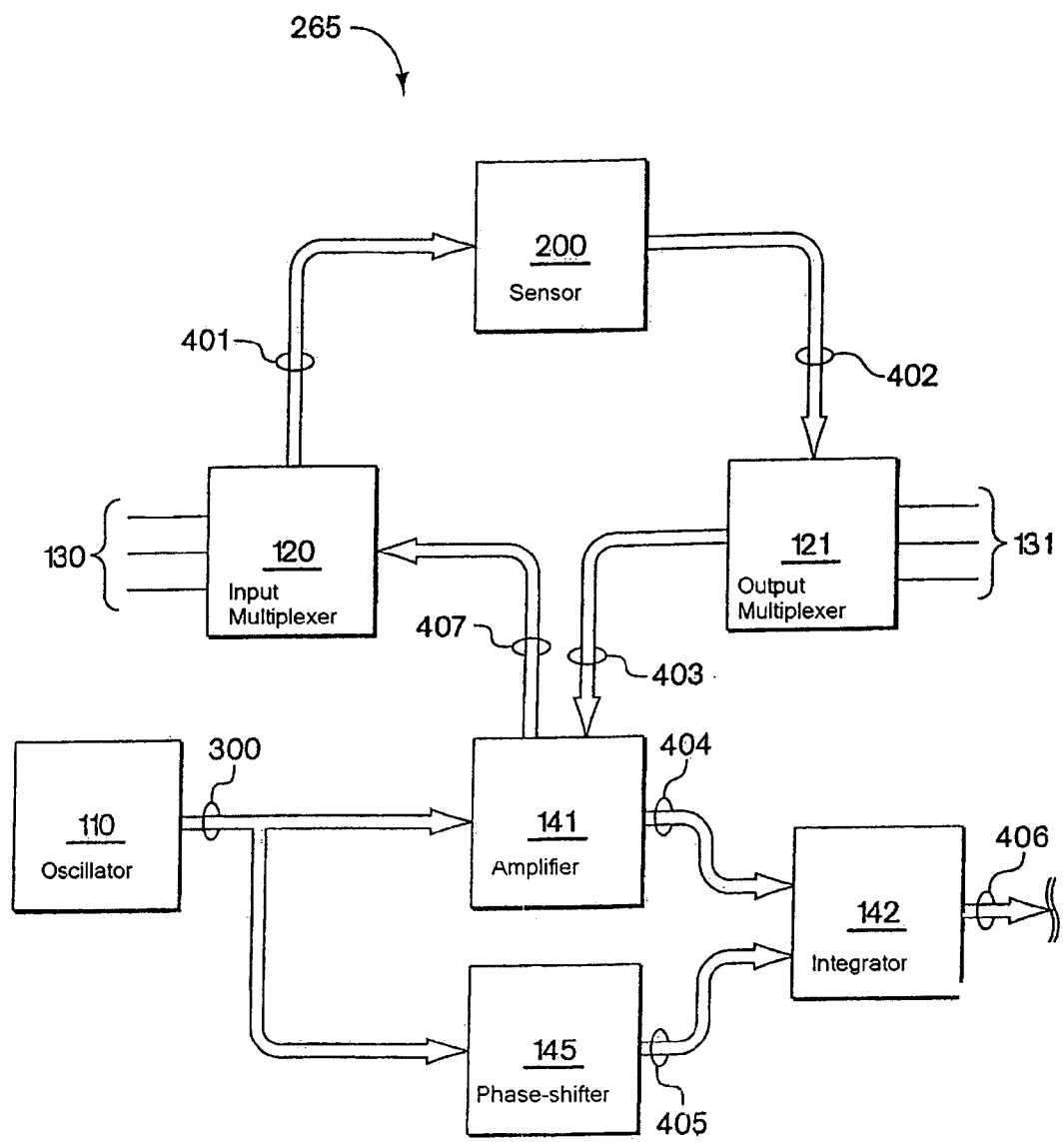
FIG. 5 illustrates a schematic representation of an exemplary system for driving and sampling a sensor array, including bias cancellation.

FIG. 5 illustrates an exemplary embodiment of a sensor system 265 having a bias-canceling capability. In some embodiments it is advantageous to cancel a bias due to the driving oscillator signal so that a sensed sensor signal may be better amplified and discriminated from other signals. The system shown in FIG. 5 is only an illustrative embodiment, and will be described below with respect to a capacitive array scanning system, however the system is not so limited and the sensor may be a sensor other than a capacitor, as described previously.

An oscillator 110 provides an oscillator signal 300, as mentioned earlier. The oscillator signal 300 is amplified using amplifier 141 to produce an amplified input signal 407. The amplified input signal 407 is provided to input multiplexer 120 as previously described and the input multiplexer 120 subsequently provides a sensor input signal 401 based on data at input select lines 130.

FIG. 5 illustrates a single sensor 200 rather than an entire sensor array such as a capacitive array 100 discussed earlier. However, it should be understood that one or more sensors or an array of such sensors may receive an input signal such as an array input signal or, in the present embodiment, a sensor input signal 401 from the input multiplexer 120.

As discussed previously, sensor 200 will provide a sensor output signal 402 based on the sensor input signal 401 and corresponding to a sensed stimulus, such as force, pressure, etc. The sensor output signal 402 is received by an output multiplexer 121 which selects the particular sensor 200 from among a plurality of sensors in a sensor array such as a capacitive sensor array 100 (not shown). The output multiplexer 121 selects the sensor output signal 402 on the basis of data presented on output select lines 131. The selected data 403 is provided from the output multiplexer 121 to the amplifier 141 and may form a feedback loop as previously described. The amplifier 141 provides an amplified output signal 404 which typically corresponds to the selected signal 403 and being amplified in its magnitude.

In the embodiment shown if FIG. 5, the amplified output signal 404 is further processed rather than merely being delivered to an amplitude detector. Here, a second branch of the oscillator signal 300 is received by a phase-shifter 145 which provides a phase-shifted signal 405. Both the amplified output signal 404 and the phase-shifted signal 405 are input to an integrator 142 that substantially sums the two signals 404 and 405.

The integrator 142 may integrate the signals 404 and 405 over several cycles of the oscillator. The integrator 142 provides a time-integrated signal 406 as an output. The integrator 142 may comprise a summing circuit having an amplifier and an integrating feedback capacitance. The symbol at the output of the integrator 142 indicates that the sensing system 265 may comprise only a portion of a larger overall sensing system such as a capacitive array scanning system.

Figure 6:
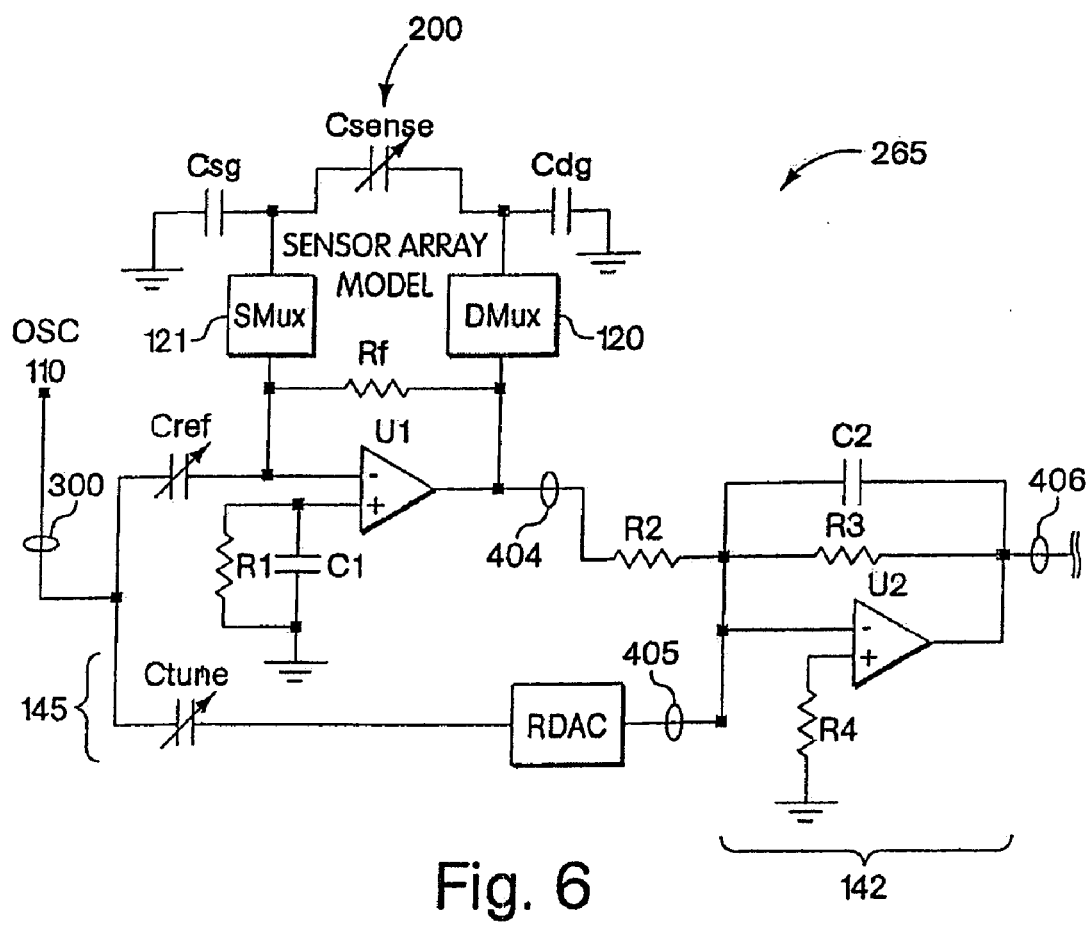
FIG. 6 illustrates an exemplary circuit for driving and sampling a sensor array, including a feedback loop and bias cancellation capability.

FIG. 6 illustrates a more detailed example of a sensor system 265 similar to that described above in FIG. 5. In this embodiment, a charge amplifier circuit is disclosed having a variable capacitance sensor Csense 200 which has a variable capacitance in response to applied pressure on the sensing capacitor 200. A sine wave oscillator 110 provides an oscillator signal 300 to the sensor 200 and to the rest of the charge amplifier circuit 265. The oscillator signal 300 passes through a reference capacitor Cref and is provided to the sensing capacitor 200 through a drive multiplexer 120 (DMux). The sensing capacitor 200 then provides a sensor output signal corresponding to the stimulus to the select multiplexer 121 (SMux). Amplifier U1 operates as amplifier 141 in the previous figures. Thus, a feedback loop between the sensing capacitor 200 and amplifier U1 going through multiplexers 120 and 121 is created.

A bias cancellation circuit is provided by use of bias-canceling capacitor Ctune and gain-adjusting capacitor Gref. The bias-canceling capacitor is adjusted at the time of manufacture and is set in a way such as to cancel or reduce the AC amplitude of the driving carrier signal 300. Oscillator signal 300 passes through the branch containing capacitor Cref to the inverting input of amplifier U1, while capacitor Ctune operates as a filter to shift the phase of the oscillator signal 300 at the output of the resistive digital to analog converter (RDAC). In this way capacitor Ctune and RDAC form a phase shifter as was described by block 145 in FIG. 5 above.

The output of amplifier U1 is provided through resistor R2 to an integrator circuit formed by amplifier U2, capacitor C2 and resistor R3. The phase-shifted signal provided by the series combination of Ctune and RDAC is also provided to the inverting input of amplifier U2. The non-inverting input of amplifier U2 is coupled to ground through a resistor R4. Capacitor C2 and resistor R3 form a feedback impedance around amplifier U2 thus integrating the input signals at the input of amplifier U2. The integrator circuit, mentioned previously as block 142 in FIG. 5, can also be considered a summing circuit which sums (a) the amplified output 404 and (b) the phase-shifted oscillator output signal 405.

According to some aspects, the arrangement presented in FIG. 6 linearizes the system's response in the presence of a nonlinear sensor 200. The sensor loop including the feedback described previously make the output of the sensing circuit correspond linearly to the stimulus (e.g., pressure capacitor gap, etc.) rather than the nonlinear relationship traditionally provided in sensor circuits responding directly (rather than inversely) to capacitance changes. Thus, the feedback loop acts as a nonlinear transformer that counteracts the nonlinear behavior of the sensor 200 to yield a linearized output.

In some embodiments, the oscillator 110 is a single polarity excitation source providing a stabilized sinusoidal waveform with a frequency in a range from 1 kHz to several megahurtz, for example from 50 kHz to 100 kHz, depending on the rest capacitance of the sensing capacitor 200 and other design considerations such as a tradeoff between sensor range, sensitivity and linearity.

The capacitive sensor 200 or a sensor array 100, represented in FIG. 6 by Csense, commonly also comprises parasitic capacitances to ground represented as Csg and Cdg. Parasitic capacitance Csg represents the parasitic capacitance from the sensor line to ground. Parasitic capacitor Cdg represents the parasitic capacitance between the drive lines and ground. To reduce or eliminate parasitic capacitance, a sensor 200 or a portion of a sensory array which is idle (not being driven or sampled) is coupled to ground to prevent parasitic capacitance effects from influencing the measurements of the non-idle sensors. In some aspects this shunting to ground of the parasitic capacitance improves system throughput, linearity and bandwidth.

Capacitor Cref is normally selected to be a multiple of Csense, for example Cref may have a value equal to three times the value of Csense. The ratio of capacitors Cref over Csense multiplied by the excitation amplitude of the oscillator determines the magnitude of the output of amplifier U1. Thus, as Csense is increased the output of amplifier U1 will decrease with a sensitivity dictated by the design of the sensing capacitors Csense.

Other design considerations determine the nature of amplifier U 1 characteristics that can be selected for the appropriate gain bandwidth and to minimize phase lag effects.

Furthermore, the driving and sensing lines to and from the sensor array 100 may be individually shielded. In this way it is possible to prevent cross-capacitance effects between the individual lines from impacting the measured capacitance due to effects such as twisting or bending of the cable bundle running to or from the array 100.

It may be advantageous in some aspects to physically place any tunable filter elements near the sensor elements 200 to provide common mode rejection to environmental effects such as temperature changes.

As described previously, combining a phase-shifted signal through the capacitor Ctune with the output of amplifier U1 in the integrator or summing amplifier U2 makes the sensor's sensitivity positive, or in other words inverts the polarity, and allows for bias cancellation. Capacitor Ctune provides any necessary phase lag adjustment while the RDAC acts as a digital potentiometer to allow for precise bias trimming for each sensor element 200. The value of the RDAC is adjusted based on a measurement at the output of summing amplifier U2 with the sensor 200 and its rest capacitance state. Such an adjustment is used to provide sufficient trim for both the bias and gain of each sensor element 200 having similar geometry or electrode surface area.

According to some aspects of the invention, the above-described sensor circuit adjustment may simplify the calibration process. Calibration is normally performed in an iterative process and is time consuming. The present design may also reduce the intervals required between calibration procedures.

Resistor Rf is a feedback resistance and in some embodiments provides stability to the circuit. Rf may also be selected to optimize the sensitivity and linearity of the sensing circuit and in some embodiments improve the settling time to increase the throughput of large sensor arrays.

As mentioned earlier, the oscillator 110 may provide a variety of oscillator signals 300. Such signals may be used as excitation waveforms which can be sinusoidal as well as non-sinusoidal waveforms. Also, dual polarity excitation is possible if its use is advantageous to a particular circuit design.

An alternative embodiment allows for the deletion of any or all of resistors R1, R4 and capacitors C1 and C2.

The output of the sensing circuit 265 FIG. 6 is provided in some embodiments to an input of an AC to DC conversion circuit such as a rectifier and to a second stage amplification circuit before amplitude detection is performed.

Figure 7:
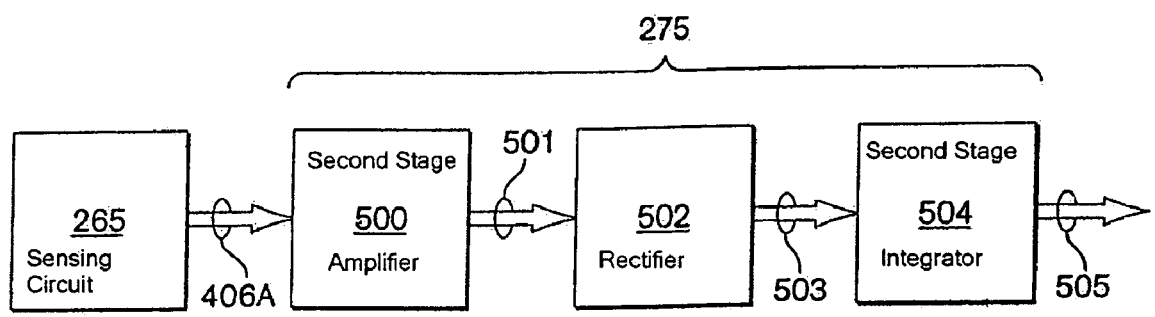
FIG. 7 illustrates a schematic representation of an exemplary second stage amplification and rectification apparatus which can be used with sensor arrays.

FIG. 7 illustrates an exemplary embodiment of a second stage circuit 275 which may be employed downstream of the previously-described sensing circuit 265. The sensing circuit 265 provides a sensing circuit output signal 406A, which may be the same as the integrated signal 406. This signal 406A contains information from the sensing element 200 indicative of the measured stimulus as well as any remaining bias, noise and other signal artifacts provided from the sensing circuit 265. The sensing circuit output signal 406A is provided to a second stage amplifier 500 which amplifies the signal corresponding to the desired measurement. In some embodiments this signal 406A may comprise an AC sinusoidal signal having an amplitude of approximately 200 mV and a frequency of approximately 50-100 kHz.

An output signal 501 from the second stage amplifier 500 is provided to a rectifier 502. The rectifier 502 is constructed in any appropriate way and converts an AC signal to a DC signal. A rectified signal 503 is provided to a second stage integrator 504 which integrates signal 503 over several cycles in time. According to some aspects, using the second stage integrator 504 instead of a low pass filter stage provides improved response time and avoids the need to wait until transients decay as is the case in low pass filter circuits. Integration in the integrator 504 is carried out over approximately 10 cycles in some embodiments.

Figure 8:
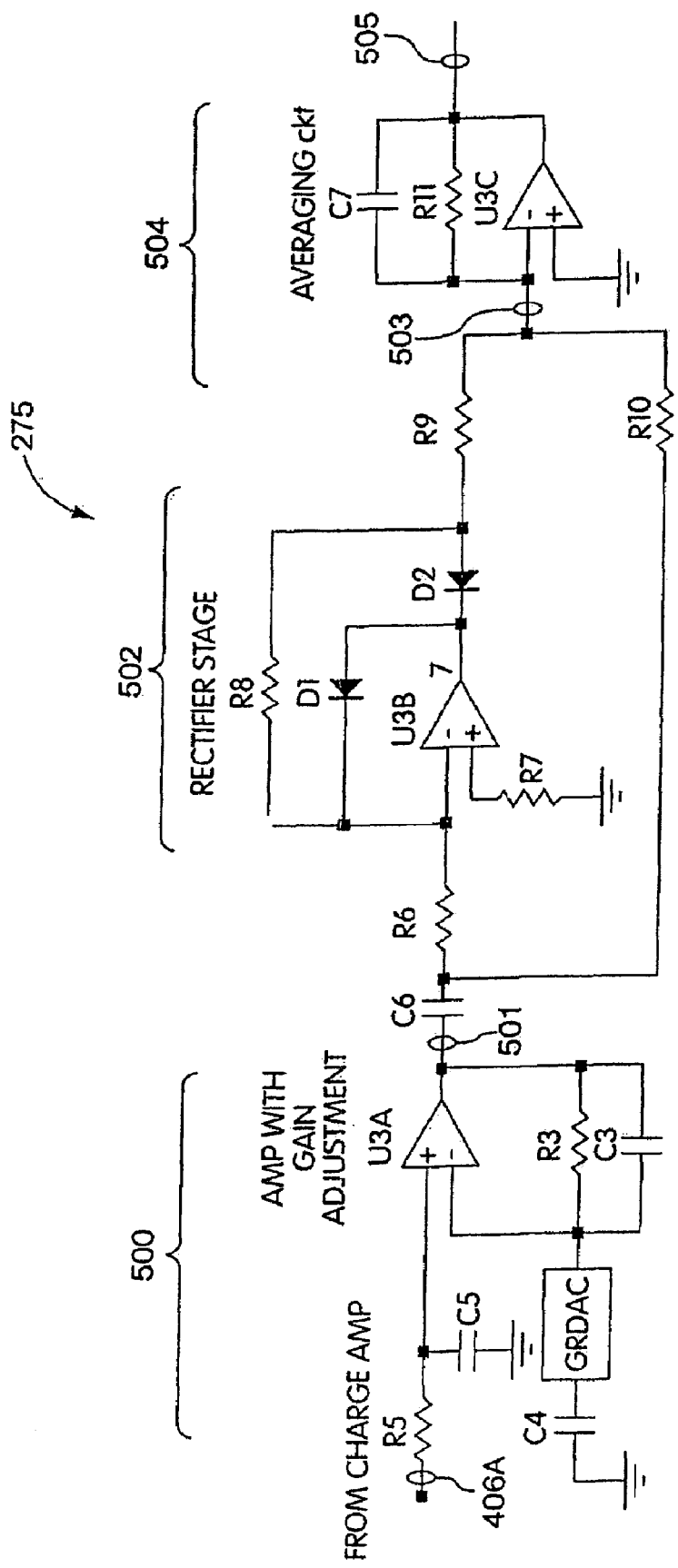
FIG. 8 illustrates an exemplary circuit according to the schematic representation of FIG. 7.

FIG. 8 illustrates one embodiment of a second stage amplification circuit 275 similar to that described in FIG. 7. A sensing circuit output signal 406A is received from a sensing circuit such as circuit 265. The signal 406A represents an output from a charge amplifier circuit which is oscillating at substantially the same frequency as the oscillator signal 300. The signal 406A is received from R5, the output of which is coupled to ground through a capacitor C5 that acts as a filter.

A second stage adjustable gain amplifier U3A receives a non-inverting input from signal 406A. The amplifier U3A is configured to provide an appropriate mid-band gain at the excitation frequency while maintaining approximately unity gain at very low frequencies. The mid-band gain is adjustable via the gain resistive digital-to-analog converter (GR-DAC). Capacitor C4 ensures that the gain near DC frequencies is low or approximately unity.

Following the second stage amplification circuit 500 a signal 501 is provided to a rectifier stage 502. The rectifier stage 502 comprises an amplifier U3B and performs precision full-wave rectification, especially at the excitation frequencies, including rectification for low input amplitude levels.

The output of rectifier stage 502 is delivered on line 503 to averaging circuit 504. Averaging circuit 504 comprises amplifier U3C and outputs an averaging circuit output 505 that is substantially a DC signal corresponding to the stimulus delivered from the sensor 200. The overall circuit of FIG. 8 represents an exemplary system for performing AC to DC conversion of the amplitude modulated signal from the charge amplifier circuit 265 shown in FIG. 6. The circuits provided above perform their function without requiring a switching element as in numerous existing synchronous phase demodulator circuits.

Note that by reversing the polarity of the diodes D1 and D2 of the rectifier stage 502 the rectifier stage 502 can be configured to provide gain for negative or positive inputs and removing the RIO path can provide for half-wave rectification.

The output of the second stage amplification circuit 275 may be an AC signal 505 having an amplitude of 4VAC and a modulation of 2V, reflecting the measured signal and having a frequency of 50 to 100 kHz. Such a signal provides a better basis for measurement of variable, but substantially DC, modulation signals from the sensor elements 200.

Some embodiments of the present invention incorporate one or more of the above-described aspects into a system which is coupled to an organism and detects physical parameters or properties of the organism. Time-series collection of biological data is one example of such an embodiment. For example, the circuits and methods described above may be used in conjunction with a catheter or other device, including non-invasive devices or minimally-invasive devices to collect biological data on a human or animal patient. Pressure profiles measured within an orifice or a cavity in time and/or space can be collected for presentation to a user or machine for storage, processing, or analysis. This may form a basis for a diagnosis of some medical condition or be used as a predictor for some other condition of the organism.

In one embodiment, a series of sensors arranged substantially in a linear form factor, are placed within a body cavity such as the esophagus and measure pressures in this cavity as a function of time. These esophageal pressures may then be displayed graphically on a graphical display, showing the physiological sequence of an action such as coughing or swallowing.

Yet another aspect of the present invention permits the use of the above-described systems and methods to obtain high-resolution measurements of large regions of interest. Some embodiments of the invention utilize several sensor array grids, each having its own sensor driving and sampling electronics, as described above, to carry out simultaneous or sequential measurements. Multiplexing electronics are used in some embodiments to collect data from the multiple sensor arrays. These embodiments may in some regards be considered scalable or parallel implementations of the concepts described above.

As an example, consider the case where a large region of interest is to be covered by sensors which collect data regarding a stimulus, e.g. pressure. The number of sensor elements will depend on the resolution required (i.e. the grid spacing) and the overall area of the region of interest. If the grid spacing is tight (fine resolution) then the number of sensor elements becomes large. In this case, interrogating or diving and sampling of each of the large number of sensors might entail cycling through the sensors in the manner described above. For a large number of sensors this can become time-consuming and slows down the sampling rate possible for sampling each member of the array. To increase the sampling rate or to increase the possible resolution for a given sampling rate or to increase the overall area that can be sampled at some resolution at a given sampling rate the region of interest may be broken into adjacent (tiled) sub-regions. Each of the sub-regions can be covered by a sensor array as described earlier, and the output from each of the sub-regions can be read by a circuit such as a multiplexer that switches between each of the sub-regions in turn.

It can be appreciated that this technique can be used in an iterative fashion, thus nesting or scaling up or down the overall sensing system so that an almost arbitrary area or resolution or sampling rate can be obtained, depending on the need. That is, in some aspects temporal performance or spatial performance may be procured at the cost of additional hardware or processing sensor electronics.

Having thus described several aspects of at least one embodiment of this invention, it is to be appreciated that various alterations, modifications, and improvements may occur to those skilled in the art. Such alterations, modifications, and improvements are intended to be part of this disclosure, and are intended to be within the spirit and scope of the invention. Accordingly, the present description and drawings are given by way of example only.

What is claimed is:

1. A sensor system, comprising:
    a sensor array having a plurality of sensor elements;
    an input multiplexer and an output multiplexer configured to select a sensor element; and
    an amplifier, disposed in a feedback arrangement around the sensor element and the input and output multiplexers, the amplifier receiving an input signal corresponding to an output of the sensor element and providing an output signal that drives the sensor element, wherein each sensor element has an individually-controlled gain or an individually-controlled offset.

2. The system of claim 1, wherein the sensor element comprises a capacitive sensor element and the sensor array comprises a capacitive sensor array.

3. The system of claim 1, wherein the sensor array comprises a first set of conductive strips crossing a second set of conductive strips to form each of the plurality of sensor elements at an intersection of a strip in the first set and a strip in the second set, the sensor array adapted and configured such that a stimulus alters a separation between a first conductive strip of the first set and a second conductive strip of the second set.

4. The system of claim 1, wherein the sensor array senses any of a force, a weight, a pressure and a displacement.

5. The system of claim 1, further comprising an amplitude detector which receives an output signal from the amplifier.

6. The system of claim 1, further comprising a nonlinear transformer which transforms a nonlinear output of the amplifier into a corresponding substantially-linear signal representing the stimulus.

7. The system of claim 6, wherein the nonlinear transformer is a feedback loop comprising the sensor element.

8. The system of claim 1, wherein the amplifier's output signal is one of a plurality of signals which drive the sensor element.

9. The system of claim 1, further comprising a filtering circuit comprising a digitally-controlled integrator coupled to receive the output signal of the amplifier.

10. The system of claim 1, wherein a tunable filter element is coupled to the sensor element and wherein the tunable filter element is placed in physical proximity to the sensor elements to provide common mode rejection to environmental effects.

11. The sensor system of claim 1, further comprising a resistor disposed in the feedback arrangement in parallel with the selected sensor element.

12. A sensor system, comprising:
a sensor array having a plurality of sensor elements;
at least one sensor element of the sensor array, having addressable connections designating the sensor element, that senses a stimulus;
an amplifier, disposed in a feedback arrangement around the sensor element, the amplifier receiving an input signal corresponding to an output of the sensor element and providing an output signal that drives the sensor element;
a tunable filter, coupled to an oscillator having an oscillator signal, which shifts a phase of the oscillator signal to provide a phase-shifted signal; and
a summing circuit which sums the amplifier output with the phase-shifted signal to substantially cancel out oscillator bias in a portion of the sensor system.

13. The system of claim 1, further comprising a path from the sensor element to a common potential which is selectably coupled to the sensor element.

14. The system of claim 1, wherein the sensor element is selectably coupled to a ground potential when the sensor element is not being driven or sampled.

15. The system of claim 1 wherein the sensor element is coupled to an electrical line which is individually shielded from electromagnetic effects.

16. The system of claim 1, further coupled to at least one other sensor system such that the system of claim 1 and the at least one other sensor system cover a combined region of interest having a greater area than an area covered by the system of claim 1 or an area covered by the at least one other sensor system.

17. A method for measuring a stimulus on a sensor array, the sensor array comprising a first set of conductive strips crossing a second set of conductive strips to form a plurality of sensor elements, the method comprising, for each of a plurality of the sensor elements:
selecting the sensor element of the sensor array associated with a first conductive strip of the first set of conductive strips and a second conductive strip of the second set of conductive strips, the selecting comprising selecting the first conductive strip and the second conductive strip and an offset based on the selected sensor element;
generating a sensor element output signal on the first conductive strip, the sensor element output signal being representative of a distance between the first conductive strip and the second conductive strip;
amplifying the sensor element output signal to generate an amplified signal representative of a pressure on the sensor element with the selected offset; and
feeding back the amplified signal to the second conductive strip.

18. The method of claim 17, wherein:
the sensor has a non-linear response; and
feeding back the amplified signal comprises feeding back the amplified signal through a non-linear transformer feedback loop corresponding to the non-linear sensor response.

19. The method of claim 18, wherein the non-linear sensor response is a non-linear response to a pressure applied to the sensor element.

20. The method of claim 17, further comprising selectively coupling at least one sensor element in the sensor array to a common potential during a time period in which the selected sensor element is idle and at least one other sensor elements is being sampled.

21. The method of claim 20, wherein the common potential is a ground potential.

22. A method for measuring a stimulus on a sensor array composed of a first set of conductive strips crossing a second set of conductive strips to form a plurality of sensor elements, comprising:
selecting a sensor element of the sensor array associated with a first conductive strip of the first set of conductive strips and a second conductive strip of the second set of conductive strips;
generating a sensor element output signal on the first conductive strip;
amplifying the sensor element output signal to generate an amplified signal representative of a physical property;
feeding back the amplified signal to the second conductive strip;
providing an oscillating signal to drive the sensor element,
shifting a phase of the oscillating signal to provide a phase-shifted signal; and
summing the sensor element output and the phase-shifted signal to substantially cancel out oscillator bias in a portion of the sensor system.

23. A sensor system having an output indicating a sensed property, comprising:
a sensor array having a plurality of sensor elements;
an input multiplexer and an output multiplexer configured to select a sensor element;

an amplifier, disposed in a feedback arrangement around the sensor element and the input and output multiplexers, the amplifier receiving an input signal corresponding to an output of the sensor element and providing an output signal that drives the sensor element; and an amplitude detector having an input and an output, the input being coupled to receive the output signal of the amplifier, the output of the amplitude detector being coupled to the output of the sensor system.

24. The sensor system of claim 23, wherein each of the sensor elements comprises a capacitive sensor and the amplitude detector comprises a non-linear element.

25. The sensor system of claim 24, wherein the amplitude detector comprises a rectifier.

26. The sensor system of claim 23, further comprising:
    a summing circuit; and
    an integrator stage,
wherein the input of the amplitude detector is coupled to receive the output signal of the amplifier through the summing circuit, and the output of the amplitude detector is coupled to the output of the sensor system through the integrator stage.

27. The sensor system of claim 26, further comprising an oscillator driving the selected sensor element, the oscillator also being coupled to the input of the summing circuit through a phase shifting circuit.

28. The sensor system of claim 27, wherein:
    the amplifier is a first amplifier; and
    the sensor system further comprises a second amplifier, the second amplifier being connected between the summing circuit and the amplitude detector.

29. The sensor system of claim 28, further comprising a resistor connected in parallel to a selected sensor element in the feedback arrangement.

* * * * *